United States Patent [19]

Mathison et al.

[11] 4,059,586

[45] Nov. 22, 1977

[54] 5-ALKOXY-2-ALKYL-1,2,3,4-TETRAHYDROISOQUINOLENE-8-CARBOXALDEHYDE AND DERIVATIVES

[75] Inventors: Ian William Mathison; William Ebenezer Solomons, both of Memphis, Tenn.; Raymond Henry Jones, Northport, N.Y.

[73] Assignee: Marion Laboratories, Inc., Kansas City, Mo.

[21] Appl. No.: 689,078

[22] Filed: May 24, 1976

Related U.S. Application Data

[62] Division of Ser. No. 455,600, March 28, 1974, Pat. No. 3,978,067.

[51] Int. Cl.$^2$ ............................................. C07D 217/24
[52] U.S. Cl. ............................. 260/287 D; 260/289 D
[58] Field of Search ...................... 260/287 D, 289 D

[56] References Cited

U.S. PATENT DOCUMENTS 3,583,994  6/1971  Mathison .................. 260/287 D

Primary Examiner—Paul M. Coughlan, Jr.
Attorney, Agent, or Firm—Merriam, Marshall, Shapiro & Klose

[57] ABSTRACT

Provided are novel 5-alkoxy-2-alkyl-1,2,3,4-tetrahydroisoquinolines of the formula

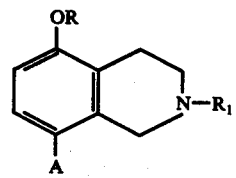

wherein A is CHO—, HOOC—CH=CH—, or HOOC—CH$_2$—CH$_2$—, R and R$_1$ are the same or different lower alkyl groups, and acid addition salts and quaternary ammonium salts thereof.

6 Claims, No Drawings

5-ALKOXY-2-ALKYL-1,2,3,4-TETRAHYDROISOQUINOLENE-8-CARBOXALDEHYDE AND DERIVATIVES

This is a division of application Ser. No. 455,600, filed Mar. 28, 1974, now U.S. Pat. No. 3,978,067 issued Aug. 31, 1976.

This invention relates to novel chemical compounds and their production. More particularly, this invention provides novel tetrahydroisoquinolines, processes for producing the compounds, novel intermediates useful in making the compounds, and novel pharmaceutical compositions containing the compounds useful for effecting desirable pharmacological activity in animals.

According to one aspect of the subject invention there is provided novel 5-alkoxy-2-alkyl-7,8-cyclpentano[h]1,2,3,4-tetrahydroisoquinoline-1'-ones of the formula

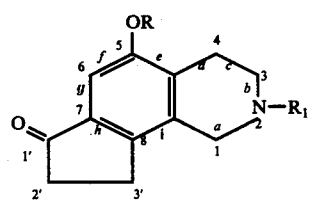

Formula I wherein R is a straight or branched chain lower alkyl group having 1 to 6 carbon atoms such as the methyl, ethyl, propyl, isopropyl, butyl and amyl groups and $R_1$ is a straight or branched chain lower alkyl group having 1 to 6 carbon atoms such as the methyl, ethyl, propyl, isopropyl, butyl and amyl groups and acid addition salts and quaternary ammonium salts thereof.

The compounds of Formula 1 are prepared by converting a 5-alkoxy-2-alkyl-1,2,3,4-tetrahydroisoquinoline by means of a Friedel-Crafts reaction to a 5-alkoxy-2-alkyl-1,2,3,4-tetrahydroisoquinoline-8-carboxaldehyde, reacting the aldehyde with malonic acid to form a β-(5-alkoxy-2-alkyl-1,2,3,4-tetrahydroisoquinoline-8) propenoic acid, catalytically reducing the propenoic acid compound to form the β-(5-alkoxy-2-alkyl-1,2,3,4-tetrahydroisoquinoline-8) propanoic acid and then effecting ring closure of such compound, such as by means of polyphosphoric acid. This process can be represented as follows:

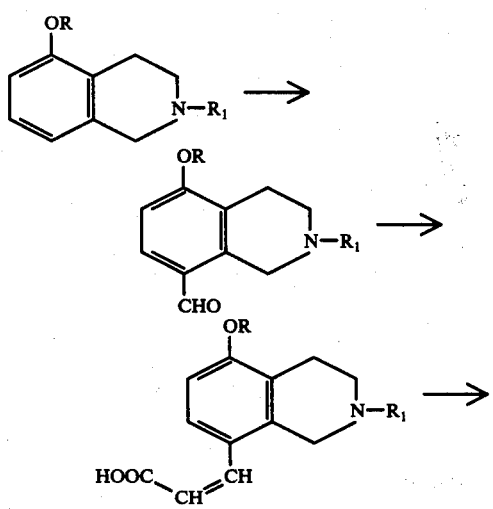

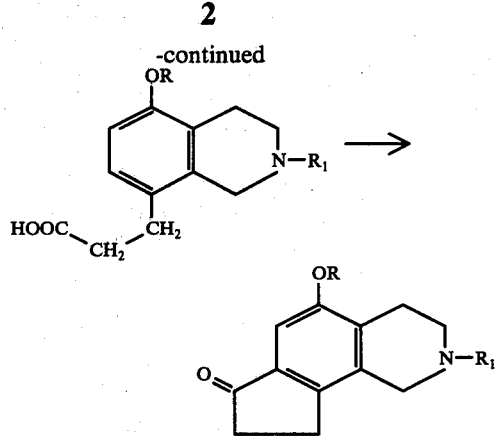

wherein R and $R_1$ have the previously assigned significance.

Among the 5-alkoxy-2-alkyl-1,2,3,4-tetrahydroisoquinolines which can be used in the process as starting materials are 5-methoxy-2-methyl-1,2,3,4-tetrahydroisoquinoline, 5-methoxy-2-methyl-1,2,3,4-tetrahydroisoquinoline, 5-line, ethoxy-2-ethyl-1,2,3,4-tetrahydroisoquinoline and 5-propoxy-2-propyl-1,2,3,4-tetrahydroisoquinoline. Durand et al., Bull. Soc. Chim, France, 270 (1961) discloses the preparation of 5-methoxy-2-methyl-1,2,3,4-tetrahydroisoquinoline.

Other such compounds, including those just named, can be prepared by the same process from the appropriate reactants. In addition, the preparation of the starting materials is well within the ordinary skill of an organic chemist.

Formylation of the 5-alkoxy-2-alkyl-1,2,3,4-tetrahydroisoquinoline starting material is readily effected according to the method of Alfred Reiche et al. in Chem. Ber., 93, 88 (1960) using a Friedel-Crafts catalyst such as stannic tetrachloride, aluminum trichloride or titanium tetrachcloride and α, α-dichloromethyl methyl ether followed by the addition of water. Some of the novel products which are produced as described are 5-methoxy-2-methyl-1,2,3,4-tetrahydroisoquinoline-8-carboxaldehyde, 5-methoxy-2-ethyl-1,2,3,4-tetrahydroisoquinoline-8-carboxaldehyde, 5-ethoxy-2-ethyl-1,2,3,4-tetrahydroisoquinoline-8-carboxaldehyde and 5-propoxy-2-propyl-1,2,3,4-tetrahydroisoquinoline-8-carboxaldehyde.

Conversion of the 5-alkoxy-2-alkyl-1,2,3,4-tetrahydroisoquinoline-8-carboxaldehyde by reaction with malonic acid in pyridine in the presence of piperidine as a catalyst at an elevated temperature, according to the Doebner modification of the Perkin reaction (Johnson "Organic Reactions" Vol. I, 226–234, John Wiley & Sons, N.Y. 1942) yields β-(5-alkoxy-2-alkyl-1,2,3,4-tetrahydroisoquinoline-8) propenoic acid. Among the compounds which are produced in this way are β-(5-methoxy-2-methyl-1,2,3,4-tetrahydroisoquinoline-8) propenoic acid, β-(5-methoxy-2-ethyl-1,2,3,4-tetrahydroisoquinoline-8) propenoic acid, β-(5-methoxy-2-ethyl-1,2,3,4-tetrahydroisoquinoline-8) propenoic acid and β-(5-propoxy-2-propyl-1,2,3,4-tetrahydroisoquinoline-β) propenoic acid.

Reduction of the unsaturated vinyl linkage in the propenoic acids is readily effected catalytically with hydrogen using palladium as the catalyst in a suitable inert liquid reaction medium containing a small amount of an acid. The hydrogenation proceeds at room temperature. After hydrogen uptake has ceased the desired β-(5-alkoxy-2-alkyl-1,2,3,4-tetrahydroisoquinoline-8) propanoic acid can be recovered by conventional methods. Among the compounds which can be produced in this way are β-(5-methoxy-2-methyl-1,2,3,4-tetrahydroisoquinoline-8) propanoic acid, β-(5-ethoxy-2-ethyl-1,2,3,4-tetrahydrosioquinoline-8) propanoic acid, β-(5-propoxy-2-propyl-1,2,3,4-tetrahydroisoquinoline-8) propanoic acid and β-(5-methoxy-2-ethyl-1,2,3,4-tetrahydroisoquinoline-8) propanoic acid.

In the next step of the process the β-(5-alkoxy-2-alkyl-1,2,3,4-tetrahydroisoquinoline-8) propanoic acid is cyclized in polyphosphoric acid according to the method of Koo, J. Am. Chem. Soc. 75, 1891 (1953) to produce 5-alkoxy-2-alkyl-7,8-cyclopentano[h]-1,2,3,4-tetrahydroisoquinoline-1'-one. The reaction is effected at a moderately elevated temperature of about 60° to 80° C. The desired product is isolated from the reaction mixture by the addition of water followed by extraction with a suitable solvent such as diethyl ether.

Among the products which are produced by the described cyclization are 5-methoxy-2-methyl-7,8-cyclopentano[h]-1,2,3,4-tetrahydroisoquinoline-1'-one, 5-ethoxy-2-ethyl-7,8-cyclopentano[h]-1,2,3,4-tetrahydroisoquinoline-1'-one, 5-propoxy-2-propyl-7,8-cyclopentano[h]-1,2,3,4-tetrahydroisoquinoline-1'-one and 5-methoxy-2-ethyl-7,8 cyclopentano[h]-1,2,3,4-tetrahydroisoquinoline-1'-one.

The 5-alkoxy-2-alkyl-7,8-cyclopentano[h]-1,2,3,4-tetrahydroisoquinoline -1'-one compounds, being tertiary amines, can be converted to acid addition salts by contacting the amines with a suitable inorganic acid such as hydrochloric acid, sulfuric acid, phosphoric acid and hydrobromic acid or an organic acid such as citric acid, acetic acid, formic acid, malic acid, fumaric acid, succinic acid, benzoic acid and tartaric acid.

Quaternary ammonium salts of the compounds are readily prepared by contacting the compounds with an alkyl halide or an alkyl sulfate, aralkyl halide or aralkyl sulfate such as methyl chloride, ethyl bromide, propyl iodide, benzyl chloride, benzyl sulfate and methyl sulfate as well as other compounds known to form quaternary ammonium salts with tertiary amines.

The 5-alkoxy-2-alkyl-7,8-cyclopentano[h]-1,2,3,4-tetrahydroisoquinoline-1'-ones are useful as neutralizing agents since they are bases which form salts with acids.

According to a second aspect of the invention, the 5-alkoxy-2-alkyl-7,8-cyclopentano[h]-1,2,3,4-tetrahydroisoquinoline-1'-ones are also useful pharmaceutically. These compounds when administered to animals parenterally or orally exert a low anti-hypertensive effect. The compounds thus can be used to reduce blood pressure.

The amount of active ingredient administered may be varied; however, it is necessary that the amount of active ingredient be such that a suitable dosage is given. The selected dosage depends upon the desired therapeutic effect and on the duration of treatment. Dosages of from 0.1 to 25 mg./kg. of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg. of active agent.

A typical tablet can have the composition:

|  | Mg |
|---|---|
| Active agent (1) | 100 |
| Starch U.S.P. | 57 |
| Lactose U.S.P. | 73 |
| Talc. U.S.P. | 9 |
| Stearic acid | 12 |

(1) 5-methoxy-2-methyl-7,8-cyclopentano[h]-1,2,3,4-tetrahydroisoquinoline-1'-one.

The compounds of Formula 1 exhibit both oral and parenteral activity and accordingly they can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

Although the end compounds of this invention are useful, they can be converted to 5-hydroxy-2-alkyl-7,8-cyclopentano[h]-1,2,3,4-tetrahydroisoquinolines which, in general, have increased anti-hypertensive activity and higher $LD_{50}$ values. This conversion can be effected by chemically reducing the 5-alkoxy-2-alkyl-7,8-cyclopentano-[h]-1,2,3,4-tetrahydroisoquinoline-1'-ones to 1'-hydroxy-5-alkoxy-2-alkyl-7,8-cylopentano[h]-1,2,3,4-tetrahydroisoquinolines, hydrogenolyzing the said compounds to 5-alkoxy-2-alkyl-7,8-cyclopentano[h]-1,2,3,4-tetrahydroisoquinolines and then cleaving the ether group to form the corresponding 5-hydroxy-2-alkyl-7,8-cyclopentano[h]-1,2,3,4-tetrahydroisoquinolines. This series of reactions can be represented as follows:

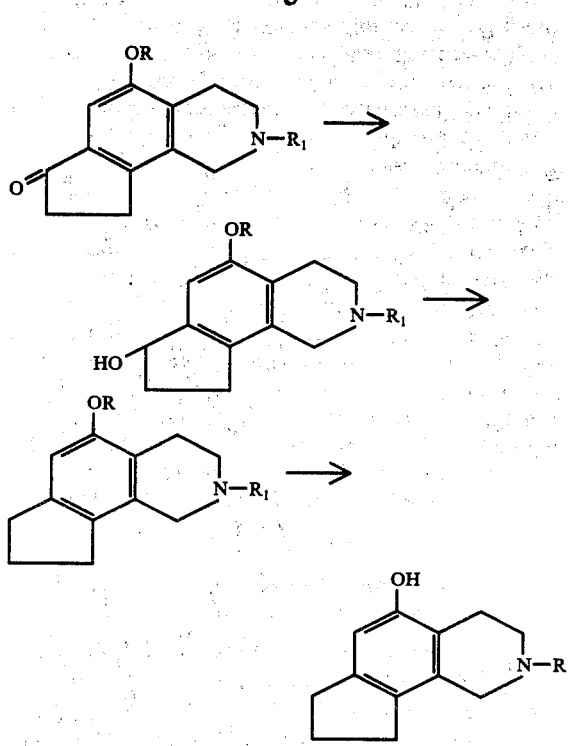

wherein R and R₁ have the previously assigned significance. In addition to 5-hydroxy-2-methyl-7,8-cyclopentano[h]-1,2,3,4-tetrahydroisoquinoline, the preparation of which in Examples 5 to 7 illustrates the described process, the following representative compounds can be produced by the same process from the appropriate starting materials: 5-hydroxy-2-ethyl-7,8-cyclopentano[h]-1,2,3,4-tetrahydroisoquinoline, 5-hydroxy-2-propyl-7,8-cyclopentano[h]-1,2,3,4-tetrahydroisoquinoline and 5-hydroxy-2-butyl-7,8-cyclopentano[h]-1,2,3,4-tetrahydroisoquinoline.

5-hydroxy-2-methyl-7,8-cyclopentano[h]-1,2,3,4-tetrahydroisoquinoline has an ALD₅₀ in mice of 100–150 mg/kg i.p. When administered as the base at 50 mg/kg i.p. to hypertensive rats the following percent change in systolic blood pressure was observed:

| 1 Hour | −18.9 ±2.8 |
|---|---|
| 2 Hours | −13.6 ±3.6 |
| 4 Hours | −11.2 ±2.6 |
| 24 Hours | −4.7 ±4.0 |

The following examples are presented to further illustrate the invention.

EXAMPLE 1

5-Methoxy-2-methyl-1,2,3,4-tetrahydroisoquinoline-8-carboxaldehyde

Into a flask equipped with a mechanical stirrer, an equilibrium addition funnel, and a condenser fitted with a calcium chloride drying tube, were placed methylene chloride (150 ml) and 5-methoxy-2-methyl-1,2,3,4-tetrahydroisoquinoline (15.0 g, 0.085 mole). The solution was cooled to 0° C and stirred. Titanium tetrachloride (51.6 g, 0.272 mole) was added gradually, followed by the rapid dropwise addition of α,α-dichloromethyl methyl ether (9.8 g, 0.085 mole). After the reaction mixture was allowed to warm to room temperature, it was refluxed for 7 hours. The titanium chloride complex of the product was decomposed with water and ice, and the resulting solution kept cool as it was made basic with excess sodium hydroxide (20%). The resulting suspension was extracted with chloroform. The extract was dried over sodium sulfate and the solvent removed, affording the crude product which was vacuum distilled (b.p. 122° C/0.1 mm) to yield 13.0 g (74%) of 5-methoxy-2-methyl-1,2,3,4-tetrahydroisoquinoline-8-carboxaldehyde. The hydrochloride salt melted at 244°–245° C after recrystallization from absolute ethanol. Anal. Calcd. for $C_{12}H_{13}NO_2Cl$: C, 59.6; H, 6.7; N, 5.8; Cl, 14.7. Found: C, 59.8; H, 6.8; N, 5.8; Cl, 14.4.

EXAMPLE 2

α-(5-methoxy-2-methyl-1,2,3,4-tetrahydroisoquinoline-8)propenoic acid hydrochloride Into a flask (100 ml) were placed malonic acid (12.0 g, 0.116 mole) and dry pyridine (25 ml). The contents of the flask were heated until solution occurred. After the solution had cooled to room temperature, 5-methoxy-2-methyl-1,2,3,4-tetrahydroisoquinoline-8-carboxaldehyde (12.0 g, 0.058 mole) was added. Piperidine (25 drops) was added as a catalyst. The reaction mixture was warmed for 30 minutes at 80° C followed by a 2½ hour refluxing. After the solution had cooled, it was poured into cold water (200 ml) and slowly collected by filtration and dried (4 hours, 110° C); it was then ground and further dried (2 hours, 110° C) in a vacuum oven. The filtrate was successively concentrated and cooled until no additional product precipitated. The β-(5-methoxy-2-methyl-1,2,3,4-tetrahydroisoquinoline-8)propenoic acid HCl, m.p. 260°–265° C (11.5 g, 70%) was not purified.

EXAMPLE 3

α-(5-methoxy-2-methyl-1,2,3,4-tetrahydroisoquinoline-8)propanoic acid hydrochloride Into a hydrogenation bottle (500 ml) were placed 5% palladium on charcoal (0.5 g) and a suspension of β-(5-methoxy-2methyl-1,2,3,4-tetrahydroisoquinoline-8)propenoic acid HCl (5.7 g, 0.028 mole) in dilute (1%) hydrochloric acid (250 ml). The compound was reduced with hydrogen at room temperature during a 20 hour period in a low pressure hydrogenation apparatus at 45 psig. After removal of the catalyst by filtration, the filtrate was successively concentrated and cooled until no further product precipitated. The portions of the product β-(5-methoxy-2-methyl-1,2,3,4-tetrahydroisoquinoline-8)propanoic acid HCl were collected by filtration and dried (4 hours, 110° C) in a vacuum oven. If the dry product (4.8 g, 84%) had a melting point less than 210° C., it was recrystallized from water (m.p. 212° C). Anal. Calcd. for $C_{14}H_{20}NO_3Cl$: C, 58.8; H, 7.1; N, 4.9; Cl, 12.4. Found: C, 58.9; H, 7.0; N, 4.7; Cl, 12.2.

EXAMPLE 4

5-methoxy-2-methyl-7,8-cyclopentano[h]-1,2,3,4-tetrahydroisoquinoline-1'-one

Into a flask (500 ml) which was heated to 55° C with an oil bath and equipped with a mechanical stirrer, calcium chloride drying tube, and a thermometer, were placed preheated (steam bath) polyphosphoric acid (PPA) (100 g) and β-(5-methoxy-2-methyl-1,2,3,4-tetrahydroisoquinoline-8)propanoic acid (7.4 g, 0.026 mole). The mixture was stirred as the temperature of the oil bath was gradually raised. At an internal temperature of 60° C the reaction commenced, as evidenced by a light green color. The internal temperature was raised to 78° C over a 15 minute period and maintained there for a further 20 minutes. The reaction mixture became dark green during this time. The PPA complex formed was then decomposed with ice and water after the contents of the flask had cooled to room temperature. The solution was kept at room temperature or cooler during basification with sodium hydroxide (20%) by the addition of large amounts of ice. The resulting suspension was extracted with diethyl ether and the extract was dried over sodium sulfate. Removal of the ether afforded the crude product 5-methoxy-2-methyl-7,8-cyclopentano[h]-1,2,3,4-tetrahydroisoquinoline-1'-one which was recrystallized (m.p. 151°–152° C) from diethyl ether (3.9 g, 65%). Anal. Calcd. for $C_{14}H_{17}NO_2$: C, 72.7; H, 7.4; N, 6.1. Found: C, 72.5; H, 7.5; N, 5.9.

The Following Examples Are Presented To Illustrate The Conversion Of The Compounds Of This Invention Into Other Useful Compounds

EXAMPLE 5

1'-Hydroxy-5-methoxy-2-methyl-7,8-cyclopentano[h]-1,2,3,4-tetrahydroisoquinoline Into a flask (1 liter) equipped with a mechanical stirrer, an equilibrium addition funnel (500 ml), and a condenser fitted with a calcium chloride drying tube was placed lithium aluminum hydride (0.72 g, 0.0190 mole) which was covered with anhydrous diethyl ether (150 ml). The contents of the flask were cooled to 0° C and stirred while an anhydrous diethyl ether solution (300 ml) of 5-methoxy-2-methyl-7,8-cyclopentano[h]-1,2,3,4-tetrahydroisoquinoline-1'-one (2.20 g, 0.0095 mole) was added dropwise rapidly. When the addition was complete, the reaction mixture was allowed to warm to room temperature, then refluxed for 5 hours. To destroy excess hydride, the following steps were taken: the contents of the flask were cooled to 0° C, diatomaceous earth filter-aid (1.5 g) was added, and ice cold water was added very slowly until the reaction mixture lost its gray color. The ether solution was then decanted and dried over sodium sulfate. Removal of the ether afforded the crude product 1'-hydroxy-5-methoxy-2-methyl-7,8-cyclopentano[h]-1,2,3,4-tetrahydroisoquinoline which was recrystallized from diethyl ether, m.p. 112.5°–113.5° C (1.95 g, 84%).

EXAMPLE 6

5-methoxy-2-methyl-7,8-cyclopentano[h]-1,2,3,4-tetrahydroisoquinoline

Into a hydrogenation bottle (500 ml) filled with nitrogen were placed 5% palladium on charcoal (0.4 g) and a solution consisting of 1'-hydroxy-5-methoxy-2-methyl-7,8-cyclopentano[h]-1,2,3,4-tetrahydroisoquinoline (1.4 g, 0.0061 mole) and ethanol (200 ml) to which had previously been added concentrated hydrochloric acid (2 ml). Hydrogenolysis occurred during a 48-hour period in contact with hydrogen in a low pressure hydrogenation apparatus. After collection of the catalyst by filtration, the filtrate was made basic with sodium hydroxide (10%). The precipitated sodium chloride was collected by filtration and the filtrate was poured into a flask (500 ml) from which the solvent was removed on an evaporator. Diethyl ether (200 ml) was added to the cooled residue. After thorough agitation of the residue in the ether, the undissolved sodium chloride was collected by filtration and the filtrate was dried over sodium sulfate. Removal of the ether afforded the product 5-methoxy-2-methyl-7,8-cyclopentano[h]-1,2,3,4-tetrahydroisoquinoline, m.p. 78°–80° C (1.30 g, 98%).

EXAMPLE 7

5-Hydroxy-2-methyl-7,8-cyclopentano[h]-1,2,3,4-tetrahydroisoquinoline hydrobromide A suspension of the hydrobromide of 5-methoxy-2-methyl-7,8-cyclopentano[h]-1,2,3,4-tetrahydroisoquinoline (2.0 g, 0.0066 mole) in hydrobromic acid (48%, 25 ml) was gently refluxed for 3 hours. The excess HBr was removed on a solvent evaporator and the residue was recrystallized from acetonitrile affording the pure product 5-hydroxy-2-methyl-7,8-cyclopentano[h]-1,2,3,4-tetrahydroisoquinoline HBr, m.p. 265°–267° C (1.1 g, 58%).

The foregoing detailed description has been given for clearness of understanding only, and no unnecessary limitations should be understood therefrom, as modifications will be obvious to those skilled in the art.

What is claimed is:

1. 5-Lower alkoxy-2-lower alkyl-1,2,3,4-tetrahydroisoquinoline-8-carboxaldehyde.
2. 5-Methoxy-2-methyl-1,2,3,4-tetrahydroisoquinoline-8-carboxaldehyde.
3. Beta-(5-lower alkoxy-2-lower alkyl-1,2,3,4-tetrahydroisoquinoline-8)propenoic acid.
4. A compound according to claim 3 in which the lower alkoxy group is methoxy and the lower alkyl group is methyl.
5. Beta-(5-lower alkoxy-2-lower alkyl-1,2,3,4-tetrahydroisoquinoline-8)propanoic acid.
6. A compound according to claim 5 in which the lower alkoxy group is methoxy and the lower alkyl group is methyl.

* * * * *

UNITED STATES PATENT AND TRADEMARK OFFICE
CERTIFICATE OF CORRECTION

PATENT NO. : 4,059,586

DATED : November 22, 1977

INVENTOR(S) : Ian William Mathison, William Ebenezer Solomons, and Raymond Henry Jones It is certified that error appears in the above-identified patent and that said Letters Patent are hereby corrected as shown below:

In the title, change "isoquinolene" to --isoquinoline--;
Column 1, line 17, change "cyclpen" to --cyclopen--;
Column 2, line 23, delete "line,";
line 38, change "tetrachcloride" to --tetrachloride--
line 62, change "β" to --8--;
Column 4, line 60, change "cylopentano" to --cyclopentano--;
Column 6, lines 14 and 36, change "α" to --β--;
line 40, change "2methyl" to --2-methyl--.

Signed and Sealed this

Twenty-eighth Day of February 1978

[SEAL]

Attest:

RUTH C. MASON
Attesting Officer

LUTRELLE F. PARKER
Acting Commissioner of Patents and Trademark